United States Patent [19]

Hart

[11] Patent Number: 5,561,131
[45] Date of Patent: Oct. 1, 1996

[54] DEFAUNATION METHOD

[75] Inventor: Frederick J. Hart, Camden, Australia

[73] Assignee: Mallinckrodt Veterinary, Inc., Mundelein, Ill.

[21] Appl. No.: 193,077

[22] Filed: Feb. 7, 1994

Related U.S. Application Data

[63] Continuation-in-part of PCT/AU92/00140, Aug. 5, 1992.

[30] Foreign Application Priority Data

Aug. 8, 1991 [AU] Australia .................... PK7658

[51] Int. Cl.⁶ .................. A01N 43/66; A61K 31/53; A23K 1/18
[52] U.S. Cl. ............................ 514/245; 424/438
[58] Field of Search ................ 514/245; 424/438

[56] References Cited

U.S. PATENT DOCUMENTS

| | | | |
|---|---|---|---|
| 2,720,480 | 10/1955 | Wolf | 167/33 |
| 2,820,032 | 1/1958 | Hill et al. | 260/249.5 |
| 3,074,946 | 1/1963 | Rattenbury et al. | 260/249.5 |
| 3,349,090 | 10/1967 | Brooms et al. | 260/268 |
| 4,183,929 | 1/1980 | Conrow et al. | 424/249 |
| 4,683,308 | 7/1987 | Gunther et al. | 544/211 |

FOREIGN PATENT DOCUMENTS

| | | |
|---|---|---|
| 47710/64 | 2/1966 | Australia . |
| 25186/67 | 1/1969 | Australia . |
| 68915/74 | 11/1975 | Australia . |
| 39771/85 | 9/1985 | Australia . |
| 336494 | 3/1989 | European Pat. Off. . |
| 1553011 | 1/1969 | France . |

OTHER PUBLICATIONS

Towne, G. et al., "Effects of supplemental tallow on rumen ciliated protozoa in feedlot cattle" *Arch. Anim. Nutr.*, vol. 41, No. 2, pp. 203–207, 1991;.

Yang, C.–M. J. and G. A. Varga, "Effect of chemical defaunation of milk production and composition by holstein cows" *J. Dairy Sci.*, vol. 72, Supp. 1, pp. 414–415, 1989;.

Supplementary European Search Report for EP 92 91 6958, 4 Jul. 1994.

PCT International Search Report for PCT/AU 92/00410 (1992).

*Primary Examiner*—José G. Dees
*Assistant Examiner*—Mary C. Cebulak
*Attorney, Agent, or Firm*—Lahive & Cockfield

[57] ABSTRACT

This invention relates to the use of triazine compounds for the preparation of a medicament for use in a method for defaunation of an animal by administering to said animal an effective amount of the compound selected. In particular the invention relates to a method for selective reduction of protozoal populations in a host animal using substituted 1, 3, 5 triazines.

53 Claims, No Drawings

DEFAUNATION METHOD

This application is a CIP of PCT/AU92/00410 filed Aug. 5, 1992.

This invention relates to the use of particular compounds for defaunation of ruminants. In particular this invention relates to a method for selective reduction of protozoal populations in a host animal by chemical means.

DESCRIPTION OF PRIOR ART

Ruminant animals may contain extremely large quantities of ciliate protozoa. Conservative estimates suggest that as much as 50% by weight of the total microbial biomass in grazing animals may be ciliate protozoa. Generally, these microorganisms enter their host in the early post-natal period of the host's life.

Protozoal organisms are transferred from host to host via saliva which is either left on pasture during grazing or transferred during the mothering process. Very high numbers of protozoal organisms are found in saliva due to regurgitation of cud by the animal. Drinking water also serves as an important vector for the spread of these microorganisms among animals. The transfer of protozoa from host to host is not limited to an intra-species relationship. Rather, it is possible for protozoal transfer to occur between other animal species if they ingest feed particles or water where faunated stock are communally grazing.

Defaunation is the selective removal of protozoa from the rumen, that is to say the removal of protozoa in preference to the removal or deactivation of bacteria. As protozoa predate on rumen bacteria and resist outflow from the rumen, they recycle a considerable amount of protein within the rumen. They also degrade dietary protein very rapidly, resulting in a non-synchronized release of nitrogen and energy for bacterial growth. The removal of protozoa results in an increase in the capture of dietary nitrogen in the rumen and improves the efficiency of feed utilization.

It appears that ruminants (e.g. sheep, goats, deer, cattle) in all physiological stages of growth and development (e.g. body growth, wool and fiber growth, pregnancy, lactation) will respond to defaunation. This may result from an increase in the protein to energy ratio of digesta reaching the animal's intestines. Defaunation allows ruminants to increase the amount of protein and energy which they extract out of their diet. Defaunation is thus believed to improve wool growth in sheep, fiber growth in goats, milk production and meat production in sheep, goats, deer, cattle and other ruminants and to otherwise enhance the value or well-being of the animals. Furthermore, by stabilizing microbial population dynamics in ruminants and by reducing methane and carbon dioxide gas production it is thought that defaunation may alleviate, if not prevent, pasture and feedlot bloat.

Previously, defaunation has been carried out with detergents. The reduction and/or removal of protozoal populations by administering detergent-based compounds to sheep has been shown to increase wool growth by 15–26%. The major disadvantage with detergent-based defaunation compounds is that sheep must be repeatedly dosed to eliminate or reduce protozoa. Repeated dosing with detergents has a two-fold effect on the treated animals. Firstly, it has a deleterious effect upon the growth of the animal and secondly it can cause weaknesses to develop in the growing wool or fiber.

In addition most surfactants effective for defaunation are highly toxic, can result in fatality and can have a high failure rate (e.g. 20%) in their ability to defaunate.

It is an object of this invention to provide a novel method of defaunation which at least in preferred embodiments avoids or ameliorates disadvantages of the prior art.

It is a second object of this invention to provide a method for increasing wool growth in sheep and fiber growth in goats.

It is a third objective of this invention to provide a new method for increasing milk quality/volume in lactating animals.

It is a fourth objective of this invention to provide a novel method for improving feed conversion efficiency, live weight gain and meat quality in ruminants.

It is a fifth objective of this invention to provide a novel method of improving reproductive performance and offspring survival in animals.

It is a sixth objective of this invention to provide a novel method of eliminating bloat in animals.

SUMMARY OF THE INVENTION

According to a first aspect, the present invention consists of a method for defaunation of a ruminant wherein said method comprises the step of administration to the ruminant of an effective amount of one or more of the compounds of formula 1

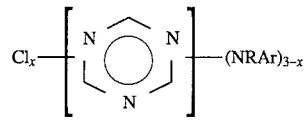

wherein:
X=1 or 2
R=H or lower alkyl
Ar=phenyl, diphenyl, napthyl, anthracyl, phenanthryl radicals and substituted derivatives thereof wherein said substituents are selected from the group consisting of aliphatic hydrocarbons, endo-aliphatic hydrocarbon, aryl hydrocarbon, nitroso, nitro, amino, chloro, bromo, iodo, hydroxyl, azo, cyano, thiocyano, alkoxy, acyloxy, aryloxy and mercaptyl groups as a principal.

The term lower alkyl is used herein to define an alkyl group containing 1 to 8 carbon atoms inclusive and includes straight and branched alkyl groups. The term loweralkyl is used herein to define an alkyl group containing 1 to 8 carbon atoms inclusive and includes straight and branched chain alkyl groups. According to a second aspect, the present invention consists of the use of a compound of formula 1

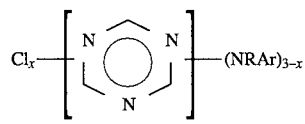

wherein:
X=1 or 2
R=H or lower alkyl
Ar=phenyl, diphenyl, Napthyl, anthracyl, phenanthryl radicals and substituted derivatives thereof wherein said substituents are selected from the group consisting of aliphatic hydrocarbons, endo-aliphatic hydrocarbon, aryl hydrocarbon, nitroso, nitro, amino, chloro, bromo, iodo, hydroxyl, azo, cyano, thiocyano, alkoxy, acyloxy, aroloxy and mercaptyl groups as a principal for the preparation of a medicament for use in a method for defaunating of an animal by administering to said animal an effective amount of said compound.

Surprisingly, it has been found that when a compound selected from the class of formula I is administered to a ruminant the said chemical compound selectively eliminates protozoa thereby enhancing the commercially valuable characteristics of the animals. By "a selective" elimination of the protozoal population it is meant that the protozoa are eliminated without substantial alteration of the ecology and population levels of other microorganisms which inhabit the rumen of ruminants.

Preferred compounds which may be used in the defaunation method are those of formula 2.

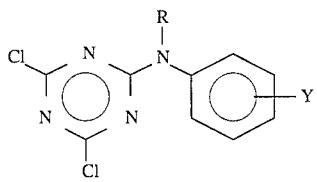

wherein

R is H or lower alkyl

Y is selected from aliphatic hydrocarbons, endo-aliphatic hydrocarbons, aryl hydrocarbons, nitroso, nitro, amino, chloro, bromo, iodo, hydroxyl, azo, cyano, thiocyano, acyloxy, aryloxy and mercaptyl groups.

The most particularly preferred compounds occur when R is hydrogen and Y is a chlorine in the two position of the phenyl ring, namely 2,4-dichloro-6-(2-chloroanilino)-1,3,5-triazine, when R is hydrogen and Y is methyl at the 2 and 4 position of the phenyl ring, namely 2,4 dichloro-6-(2,4-dimethylanilino)-s-triazine, or when R is hydrogen and Y is chlorine in the 3 position and methyl in the 4-position of the phenyl ring, namely 2,4 dichloro-6-(3 chloro-4-methylanilino)-s-triazine.

DETAILED DESCRIPTION OF THE INVENTION

The defaunating compounds of the invention are substituted 1,3,5-triazines. The preferred compounds are chloroarylamino 1,3,5-triazines. In general, the preferred compounds of the invention comprise those tri-(C-substituted) 1,3,5-triazines, wherein at least one substituent is chlorine and at least one is arylamino. While essential that there be at least one such arylamino group on the 1,3,5-triazine nucleus of the compounds of the invention, it is not intended that the meaning of the term aryl should be limited to a hydrocarbon group nor that when two such aryl groups are present that they be identical. Thus, compounds of the invention can be supplied wherein the aryl group on the exocyclic nitrogen atom is further substituted with certain other radicals described hereinafter. Furthermore, such aryl groups are not limited to phenyl as polynuclear aromatic groups might also find uses within the scope of the invention.

Substituents of the aryl group may, for example, include straight chain aliphatic radicals such as methyl, ethyl, propyl, hexyl, or dodecyl or the isomeric or branched chain equivalents thereof such as for example, isopropyl, isobutyl, sec-butyl and the various branched chain amyl, hexyl, nonyl and higher aliphatic radicals, etc. Furthermore, these aryl groups can be substituted with endo-aliphatic groups for example, methylene, ethylene, propylene and butylene to provide the corresponding phenyl endomethylene, phenyl endoethylene, hydrindene and tetralin radicals. Likewise, the aryl group can be further substituted with the same or other aryl groups.

Some examples of triazine compounds which may be used for administration in the defaunation method include:

2,4-dichloro-6-(α-naphthylamino)-s-triazine;
2,4-dichloro-6-(β-naphthylamino)-s-triazine;
2,4-dichloro-6-(toluino)-s-triazine;
2-chloro-4,6-bis(2,5-dichloroanilino)-s-triazine;
2-chloro-4,6-bis(p-nitroanilino)-s-triazine;
2-chloro-4,6-bis(p-anisidino)-s-triazine;
2-chloro-4,6-bis(chloroanilino)-s-triazine;
2-chloro-4,6-bis(anilino)-s-triazine;
2-chloro-4,6-bis(α-naphthylamino)-s-triazine;
2-chloro-4,6-bis(N-methylanilino)-s-triazine;
2,4-dichloro-6-(o-bromoanilino)-s-triazine;
2,4-dichloro-6-(2,5-dichloroanilino)-s-triazine;
2,4-dichloro-6-(o-ethylanilino)-s-triazine;
2,4-dichloro-6-(β-bromoanilino)-s-triazine;
2,4-dichloro-6-(2,4-dichloroanilino)-s-triazine;
2,4-dichloro-6-(dibromoanilino)-s-triazine;
2,4-dichloro-6-(m-bromoanilino)-s-triazine;
2,4-dichloro-6-(2,4-dichloroanilino)-s-triazine;
2,4-dichloro-6-(3-chloro-2-methylanilino)-s-triazine;
2,4-dichloro-6-(5-chloro-2-methylanilino)-s-triazine;
2,4-dichloro-6-(m-chloroanilino)-s-triazine;
2,4-dichloro-6-(o-diphenylamino)-s-triazine;
2,4-dichloro-6-(p-cyanoanilino)-s-triazine;
2,4-dichloro-6-N-(p-azobenzeneamino)-s-triazine;
2,4-dichloro-6-(p-nitroanilino)-s-triazine;

Other examples which are particularly preferred for use in the method of the invention are provided in table 1 which follows:

TABLE 1

| (COMPOUNDS BASED ON FORMULA 2). | | |
|---|---|---|
| COMPOUND # | SUBSTITUENTS (SEE FORMULA 2) | |
| | R | Y |
| 1. | H | — |
| 2. | H | 4-Cl |
| 3. | H | 4-Br |
| 4. | H | 4-OH |
| 5. | H | 4-OMe |
| 6. | H | 4-Me |
| 7. | H | 3-Cl, 4-Cl |
| 8. | H | 2-Me |
| 9. | H | 2-Me, 4-Me, 6-Me |
| 10. | H | 3-Me, 4-Me |
| 11. | H | 4-I |
| 12. | Me | 2-Me, 4-Me |
| 13. | H | 2-Me, 4-OMe |
| 14. | Me | — |
| 15. | H | 3-SMe |
| 16. | H | 3-NO2 |
| 17. | H | 3-OMe, 4-OMe |
| 18. | H | 4-SMe |
| 19. | H | 3-CN |
| 20. | H | 4-C(Me)3 |
| 21. | H | 4-CH(Me)2 |
| 22. | H | 3-I |
| 23. | H | 3-OMe |
| 24. | H | 3-Cl, 4-Cl, 5-Cl |
| 25. | H | 4-phenyl |
| 26. | H | 3-NO2, 4-Me |
| 27. | H | 3-Cl, 4-Me |
| 28. | Et | — |
| 29. | Me | 3-Cl, 4-Cl |
| 30. | H | 2-Me, 4-Me |

TABLE 1-continued (COMPOUNDS BASED ON FORMULA 2).

| COMPOUND # | | SUBSTITUENTS (SEE FORMULA 2) |
|---|---|---|
| 31. | H | 2-NO2, 4-OMe |
| 32. | H | 2-Me, 4-Me |
| 33. | Me | 4-Me |
| 34. | H | 2-Me, 4-OH, 5tBu |
| 35 | Et | — |
| 36. | H | 3,4-bicyclobutadiene, 5-OH |
| 37. | H | 2-Cl |

The selection of compounds from formula 1 which are particularly effective for the present method may be accomplished by a process of screening.

Individual compounds are first tested in vitro against protozoa and bacteria. Those compounds which are effective against the former and benign against the latter are then further tested in vivo.

It will be understood that in each case the toxicity of the compound needs to be considered in relation to the animal to which it is to be administered.

Desirably, the method of the invention is concluded by administering one or a combination of compounds according to formula 1 in a composition adapted for oral administration, for example; by combining one or more of the compounds of this invention with a suitable carrier. The composition so formed may be administered to said ruminant in either a liquid, semi-solid, capsule, tablet, or powder form. Preferably, the composition is introduced into the animal by oral means or by direct rumen injection (liquid only). Preferably the composition is introduced by combining the composition with feed.

Liquid compositions developed with compounds of this invention may comprise the said compounds dispersed in an aqueous solution. Alternatively other non-toxic liquid solvents may be used to dissolve the compounds. In addition the composition may also contain a co-solvent to assist in the dispersion of the compound(s). Typical examples of suitable co-solvents might be ethanol, DMSO or N-methyl pyrrolidone; these are used in water at a rate sufficient to give a 20% to 100% weight per volume solution. Other ingredients which may be added to the composition include: Antifoaming agents, these help prevent foaming during the manufacture of the composition; Emulsifiers, these may be added to help develop a fine dispersion; Suspending agents, such as carboxymethylcellulose, xanthan gum or polymeric silicone based agents, these may be added at a concentration at 0.01 to 5% weight per volume; Surfactants, for example any food grade material such as Teric LA 8, or ethoxylated castor oil, these may be added at a concentration of 0.01 to 20% weight per volume; A buffering system, this is used to buffer the formulation to a pH range of 4 to 8; and Preservatives, such as methyl parapen or propyl parapen or sorbic acid or benzoic acid or combination of these, which are typically added at a concentration of 0.01–5% weight per volume of the composition. The compositions used for administration to ruminants to selectively reduce protozoal populations may contain one or more of the above ingredients combined with one or more of the active compounds of this invention.

The concentration of active ingredient (i.e. the compound of formula 1) to be administered to a ruminant largely depends upon the individual animal and the active ingredient selected for use in the composition. In general, we have found that a suitable administration dose may be selected from the range of 1 to 1000 mg compound per kg of animal body weight, and preferably from 10 to 250 mg per kilogram. Typically, the range is from 70 to 167 mg per kilogram, for example, 80 to 85 mg per kilogram.

Compounds of the invention may be administered to ruminants in a single dose, or in a form which provides for a short duration sustained release or in pulse releases, preferably when pulse release administration is used the pulses are administered every 2 to 8 months, more preferably every 2 to 6 months and even more preferably every 2 to 3 months.

If a ruminant is given a single dose of a defaunation composition it may be necessary to re-dose the said ruminant every 1 to 12 months. Preferably re-dosing occurs every 2 to 8 months. More preferably re-dosing occurs every 6 months.

In some situations where a single dose of defaunation composition does not totally eradicate the protozoan infection, repeating the treatment 2 to 3 times over a 2-day to 6-day week interval should achieve total eradication. Repeating the treatment over a 2-day to 2-week period appears to optimize the treatment, with a 1-week interval being most preferable.

Where a short duration sustained release method of administration is desired then the above composition should be combined with ingredients which provide for the slow release of the formulation. Typical examples of such ingredients include a combination of wax and iron filings or gelatin which slowly release the active ingredients into the rumen of the suspected faunated animal. Such ingredients can extend the effect of the active ingredients from a few days to many weeks.

Where the active ingredient is to be administered in a capsulated or tablet form then the said capsules or tablets may be prepared by any means recognized in the art. In addition the capsules or tablets might contain one or more of the previously mentioned formulation ingredients which may potentiate the effects of the active ingredient.

Re-faunation of defaunated animals is a problem which may occur if accidental recontamination or underdosing in the first application occurs. If the possibility of re-faunation exists then it maybe necessary to frequently re-dose the said animal. As re-dosing is time consuming and costly, the use of slow release formulations may serve as an effective means of overcoming this problem. Alternatively, it may be possible to prevent accidental recontamination by separating defaunated animals from faunated animals.

Compositions containing compounds of formula 1 may be prepared by any means known in the art. For example, the compounds could be milled in the presence of a co-solvent if a liquid suspension is required.

Typical benefits obtained by using the method of this invention include an increase in the average daily gain of the particular animal, more efficient food utilization by the ruminant, improved meat quality of the ruminant, increase in milk volume by the ruminant, increase in protein utilization by the ruminant, reduction or alleviation of bloat increase in wool or hair yield in an animal bearing said wool or hair, and enhanced reproduction performance and offspring survival.

Defaunation agents when administered in accordance with the invention produce a further side affect which may be advantageous to the defaunated animal in certain circumstances. Protozoa in the rumen rapidly degrade dietary and bacterial protein releasing sulphur amino acids. These amino acids are then further degraded to produce hydrogen sulphide. Hydrogen sulphide then interacts with dietary copper to form insoluble copper sulphide which is poorly absorbed. Defaunation would be advantageous to animals living in areas where their diet is deficient in copper.

The administration of defaunation agents to animals produces a number of ecological benefits to the environment. Firstly the inventive method improves recycling of nitrogen back to the soil from defaunated stock. This is accomplished by an increase in the capture of dietary nitrogen by the bacteria which leads to a concomitant increase in faecal nitrogen excretion (the nitrogen from faunated stock could escape as ammonia). In this way defaunation improves the fertility of the soil. The second benefit to be obtained from applying the inventive method is linked to a decrease in $CH_4$ and $CO_2$ output which occurs as a direct result of removing protozoa. Ruminants are known be serious contributors to greenhouse gases so by decreasing $CH_4$ and $CO_2$ output it may be possible to reduce an animals contribution to the greenhouse effect.

The following specific examples illustrate some aspects of the present inventions. They are set forth by way of illustration and teaching only and ought to be construed as non-limiting on the scope of the present invention.

EXAMPLE 1

Method for Collecting Centrifuged Rumen Liquor for Dosing Compounds

Rumen liquor was collected from rumen fistulated donor animals by withdrawing a sample under vacuum through a rumen cannula. The tube used to withdraw the sample was fitted with a stainless-steel mesh filter (250 micron aperture) to exclude most of the feed particles. The sample was then centrifuged for 5 minutes at 2,000 g to sediment the ciliate protozoa and small feed particles. The supernatant which was collected using a vacuum pump, was then used to disperse the formulation.

Defaunation compositions were then prepared by blending together the following ingredients:

Compound: 20.2 g
Ethanol: 20 ml
Centrifuged rumen liquor: 400 ml.

EXAMPLE 2

Method for Assessing the In Vitro Activity of Defaunation Compounds Against Protozoa and Bacteria Compounds of Table 1 were tested for their toxicity against rumen ciliate protozoa by firstly isolating protozoa from rumen liquor collected from faunated animals. The rumen liquor was then centrifuged at 500 g for five minutes and the supernatant discarded. The protozoal-rich sediment was then reconstituted in McDougal's artificial saliva. Residual bacteria were suppressed by using a combination of two antibiotics at low concentration. Nitrogen and energy substrate was optimized for the protozoal preparation. At all times the protozoal preparation was maintained at 39° C. and kept anaerobic.

Sixty milligrams of each the compounds of Table 1 were dissolved in 1.2 ml of dimethyl sulphoxide and dispersed in triplicate to achieve a final concentration of 50, 150, 250 and 500 ppm. Ten milliliters of protozoal preparation was then added to each tube. After every second compound, control tubes were included which contained everything except for compound. The tubes, to which a 5 ml glass syringe was attached, were then incubated for 3 hours in a water bath at 39° C. The production of gas causes the syringe plunger to be displaced.

At the end of the incubation period, the volume of gas produced was recorded and the viability of the protozoa assessed visually using a microscope. The toxicity of the compounds to protozoa was assessed from both the reduction in gas produced relative to the control and by direct observation of the protozoa for movement of cilia.

Table 2 shows the concentration of the various compounds referred to in Table 1 required to kill all ciliate protozoa.

EXAMPLE 3

In Vitro Bacterial Gas Inhibition

Compounds of Table 1 were also tested for toxicity bacteria. This involved removing protozoa from rumen liquor by centrifugation at 2,000 g for 5 minutes and collecting the bacterial rich supernatant. Nitrogen and energy substrate was added to the bacterial preparation which was then dispensed in triplicate 10 ml volumes over the same range of compound concentrations (50, 150, 250 and 500 ppm.) referred to in Example 2. Control tubes were placed after every second compound to enable the inhibition of gas resulting from the compound to be assessed. Table 2 below shows the level of inhibition of gas production by the bacteria at the concentration known to kill protozoa. It can be seen that these compounds are selective in their mode of action, in that they are more toxic to protozoa than bacteria.

TABLE 2

IN VITRO AND IN VIVO DATA FOR THE DEFAUNATION COMPOUNDS REFERRED TO IN TABLE 1

| Compound No. | Conc Required to Kill all Protozoa (ppm.) | Bact. Gas Inhibition at the conc. required to kill protozoa | a. Mouse Safety Assessment | b. Protozoal Reduction % | c. Bacterial Viability | d. Feed Intake |
|---|---|---|---|---|---|---|
| 1 | 250 | 43 | — | — | — | — |
| 2 | 150 | 38 | Poor | 100 | Good | Fair |
| 3 | 250 | 45 | Fair | 100 | Good | Good |
| 4 | 250 | 43 | Good | 100 | Poor | Poor |
| 5 | 250 | 33 | Good | 100 | Poor | Fair |
| 6 | 150 | 40 | Poor | 100 | Okay | Okay |
| 7 | 250 | 30 | Fair | 100 | Poor | Poor |
| 8 | 250 | 43 | Good | 96 | Okay | Okay |
| 9 | 250 | 41 | Good | 88 | Good | Good |
| 10 | 250 | 55 | Fair | 100 | Good | Good |
| 11 | 250 | 71 | Fair | 84 | Okay | Good |
| 12 | 250 | 35 | — | — | — | — |
| 13 | 250 | 48 | — | — | — | — |
| 14 | 250 | 38 | — | — | — | — |
| 15 | 150 | 52 | Fair | 100 | Good | Good |
| 16 | 250 | 47 | Good | 72 | Good | Good |
| 17 | 250 | 43 | Good | 98 | Okay | Fair |
| 18 | 150 | 53 | Fair | 100 | Okay | Okay |
| 19 | 250 | 50 | Fair | 100 | Poor | Good |
| 20 | 150 | 55 | Fair | 100 | Okay | Good |
| 21 | 150 | 55 | Fair | 100 | Good | Good |
| 22 | 150 | 75 | Fair | 100 | Okay | Good |
| 23 | 150 | 50 | Fair | 79 | Good | Good |
| 24 | 150 | 67 | Good | 100 | Okay | Good |
| 25 | 150 | 53 | — | — | — | — |
| 26 | 250 | 47 | — | — | — | — |
| 27 | 150 | 67 | Fair | 100 | Okay | Okay |
| 28 | 500 | 80 | — | — | — | — |
| 29 | 150 | 41 | Fair | 98 | Good | Good |
| 30 | 150 | 33 | — | 100 | Good | Okay |
| 31 | 250 | 39 | — | — | — | — |

TABLE 2-continued

IN VITRO AND IN VIVO DATA FOR THE DEFAUNATION COMPOUNDS REFERRED TO IN TABLE 1

| Compound No. | Conc Required to Kill all Protozoa (ppm.) | Bact. Gas Inhibition at the conc. required to kill protozoa | a. Mouse Safety Assessment | b. Protozoal Reduction % | c. Bacterial Viability | d. Feed Intake |
|---|---|---|---|---|---|---|
| 32 | 150 | 35 | — | 99 | Okay | Fair |
| 33 | 250 | 33 | — | — | — | — |
| 34 | 250 | 81 | — | — | — | — |
| 35 | 150 | 12 | — | — | — | — |
| 36 | 150 | 44 | — | — | — | — |
| 37 | 250 | 57 | * | 100 | Okay | Okay |

Mouse Safety =
a. Poor - death at 840 mg/kg
  Fair - >2 mice sick
  Good - All mice normal
Protozoal Reduction =
b. Reduction of protozoa relative to predosing numbers
Bacterial Viability =
c. Poor - reduction in gas
  O.K. - same as predosing levels
  Good - increase relative to predosing levels
Feed Intake =
d. Poor - greater than 50% reduction between day 2 to day 8
  Fair - greater than 50% at day 2 but less than 50% at day 8
  O.K. - transient drop, less than 50% at day 2
  Good - no reduction
$LD_{50}$ = >4000 mg/kg (The Pesticide Manual, 9th Ed. 1991)

EXAMPLE 4

Mouse Safety Assessment

Compounds of Table 1 chosen for testing in sheep were first tested in mice for signs of toxicity. Because sheep are approximately 5 times more sensitive than mice to compounds dosed orally, the dose rates applied to mice were 5 times greater than the target dose rate of 500 ppm. in rumen liquor (83 mg/kg live weight) used for sheep. Each compound was screened at three different dose levels, high (830 mg/kg), medium (415 mg/kg) and low (217 mg/kg).

252 mg of compound was used for dilution into a high medium and low dose rate. 252 mg of compound was mixed with 3 ml of G1284 solution (4% w/v ethoxylated castor oil and 0.05% w/v simethicone), to form the high dose composition. The medium dose composition was formed by diluting 1.5 ml of the high dose with 1.5 ml of G1284 solution. The low dose composition was formed by diluting 1.5 ml of the medium dose with 1.5 ml of G1284 solution. Before the high dose could be diluted it was first manually ball milled in an effort to produce a fine suspension of the compound.

All mice were weighed before dosing to calculate the appropriate dose rate. The calculation for dose rate was:

$$\text{Dose (ml)} = \frac{\text{Mouse Weight}}{50} \times 0.5 \text{ ml}$$

Each mouse was dosed using the Gavage method. With this method the mouse is dosed orally by way of an angled hypodermic needle (18 g) with a smooth spherical end. It is gently placed down the esophagus. All care must be taken not to force the needle and injure the esophagus or dose into the lungs.

Observations were made at 10, 30, 60 and 120 minutes after dosing, then every 1 or 2 hours for the first 6 hours.

Mice were usually observed for 2 days.

Results for this assessment are detailed in Table 2. Typically, few compounds fell within the poor classification. The majority of compounds tested were either in the fair or good classification.

EXAMPLE 5

Method for Determining Protozoal Reduction in Sheep

Defaunation compositions were prepared according to the method of Example 1. Compounds selected for testing according to the following methodology are listed in Table 1.

Prior to dosing of the compound, a sample of rumen liquor (200 ml) was withdrawn to establish basal numbers of protozoa.

The sample was collected using a stomach tube, inserted into the rumen via a rumen cannula (fistulated animals) or per esophagus (intact animals). After straining the sample was well mixed using a magnetic stirrer and a 0.5 ml sample was withdrawn and added to 49.5 ml of a crystal violet stain. Protozoa were counted using a microscope and a Hawksley counting chamber.

One week after administering the compound, another rumen liquor sample was collected (as described above) and examined for the presence of protozoa. Where rumen ciliate protozoa were undetectable, a reduction or inhibition value of 100% was recorded. Results recorded for the majority of those compounds referred to in Table 1 are shown in Table 2. In general, most compounds expressed a strong inhibitory effect on protozoal populations.

EXAMPLE 6

Method for Assessing Bacterial Viability in Sheep After Administering Defaunation Compounds In order to establish what effect the compounds had on the viability of rumen bacteria, a sample of rumen liquor was collected prior to dosing of the compound. The sample was withdrawn under vacuum using a pre-warmed tube inserted into the rumen through a rumen cannula. The sample was collected in a pre-warmed (39° C.) flask, gassed with carbon dioxide and covered. Two-pre-warmed 30 ml centrifuge tubes were then filled with well mixed rumen liquor and centrifuged at 2000 rpm for 5 minutes. Half the volume of each tube was then poured into another pre-warmed tube without disturbing the sediment. Three lots of 10 ml of this rumen liquor were then pipetted into 15 ml tubes which contained 10 µL of urea solution (40% w/v and 300 µL of glucose solution (50% w/v). The urea and glucose acted as substrate for the bacteria. The tubes were then gassed with carbon dioxide, stoppered and placed in a water bath at 39° C. After 10 minutes a 5 ml glass syringe was secured into the stoppers (through which a hypodermic needle had been inserted) and the gas collected for five hours and recorded.

This bacterial viability measure was then repeated one week after dosing with each of the compounds referred to in Table 1. Defaunation compositions were prepared according to the method of Example 1. The amount of gas produced was then compared with the pre-dosing level. The criterion for classifying post-dosing bacterial viability is shown below:

Poor—reduction in post-dosing gas production relative to pre-dosing levels.
OK—post-dosing gas production the same as pre-dosing levels.
Good—increase in post-dosing gas production relative to pre-dosing levels.

Data obtained for the majority of those compounds referred to in Table 1 is detailed in Table 2. Typically few compounds had a detrimental effect on bacterial populations present.

EXAMPLE 7

Method for Assessing the Effect of Administering Defaunation Compounds on Feed Intake of the Sheep Sheep were allowed a minimum of three weeks to adapt to their ration of 900 g of oaten chaff and 100 g of Lucerne chaff. The pre-dosing level of intake for each animal was established from the mean of five days intake immediately prior to dosing. Any effects of administering the compound on feed intake was then determined by measuring the level of feed intake after dosing.

The criteria of classifying the effect on food intake are shown below.

Poor—greater than 50% reduction in feed intake during the first week after dosing.
Fair—greater than 50% reduction in feed intake on the day following dosing but less then 50% reduction one week after dosing.
OK—transient drop in feed intake which is less than 50% on the day after dosing.
Good—No reduction in feed intake following dosing.

Data obtained for the majority of those compounds referred to in Table 1 are detailed in Table 2. Generally few compounds were found to substantially effect feed intake. Most compounds had no effect whatsoever.

EXAMPLE 8

Wool Growth Effects Resultant From Compounds 27, 30 and 37 From Table 1

Seven sheep each were defaunated using a dose rate of 167 mg/kg. Compounds were administered by first mixing with 20 ml of ethanol and then with 200 ml of centrifuged rumen liquor. This solution was then administered via a flexible stomach tube directly into the rumen. The sheep were fed with a ration of 90% oaten chaff and 10% Lucerne chaff at a rate of 1000 g per day. The sheep were maintained in a defaunated state by their isolation from faunated sheep to prevent the possibility of refaunation. The sheep were allowed to adjust for 3 weeks after administering the compound before any wool growth measurements were taken.

At the start of the wool growth measurement period, a 10 cm square area of wool was removed from both sides of the sheep. After four weeks the same area was reclipped and the wool retained for scouring at the end of the trial.

The sheep then had protozoa introduced back into their rumen and were allowed to adjust for three weeks. Similarly, during the second four week period, the wool was clipped from the same patch area. The wool harvested during the two four week trial periods was then scoured of wool wax and extraneous material and weighed. The results show a highly significant improvement in wool growth (see below).

TABLE 3

WOOL GROWTH RESULTS FROM THE ADMINISTRATION OF COMPOUNDS 27, 30 AND 37 FROM TABLE 1

| Compound | Treatment* | Prot. Number (per mL × $10^3$) | Feed Intake (g) | Clean Wool** Growth (g) | Response To Defaun | Level of sig. |
|---|---|---|---|---|---|---|
| 30 | Defaun | 0 | 1400 | 2.830 | 14.6 | — |
| | Refaun | 133 | 1400 | 2.469 | | |
| 27 | Defaun | 0 | 1000 | 1.753 | 10.3 | $P < 0.0$ |
| | Refaun | 337 | 1000 | 1.589 | | |
| 37 | Defaun | 0 | 982 | 1.773 | 8.9 | $P < 0.05$ |
| | Refaun | 470 | 1000 | 1.627 | | |

*Treatment period was 4 weeks. Each animal served as its own control.
**Clean wool growth per mid-side patch.

EXAMPLE 9

Sheep Test

In this trial the effect of defaunation by compounds 27, 30 and 37 (see Table 1) after 1 and 3 weeks were examined using penned sheep.

The compounds were each administered to two sheep as a single dose at 167 mg/kg body weight. Compositions containing each compound were prepared according to the method of Example 1. Sheep were penned and fed 1000 g/day of a chaffed oaten hay and Lucerne mixture (90/10). Protozoal and bacterial viabilities were monitored along with the feed intake of the sheep according to the methods taught in Examples 2, 3 and 7. The effect of defaunation is summarized in Table 4. The results show complete elimination of protozoa can be achieved 1 week after dosing without any substantial change to bacterial viability or feed intake.

TABLE 4

EFFECT OF DEFAUNATION USING COMPOUNDS 27, 30 AND 37 (BASED ON TABLE 1) ON SHEEP

| Measurement | Sampling Structure | | |
|---|---|---|---|
| | Pre-dose | 1 Week | 3 Week |
| COMPOUND 27 | | | |
| Protozoal Nos. (per mL × $10^3$) | 950 | 0 | 0 |
| Bacterial gas production (Ml per 5 hr) | 2.9 | 3.5 | 3.8 |
| Feed Intake (g/day) | 966 | 1000 | 1000 |
| COMPOUND 30 | | | |
| Protozol Nos. (per mL × $10^3$) | 346 | 0 | 0 |
| Bacterial gas production (Ml per 5 hr) | 4.4 | 1.9 | 4.6 |

TABLE 4-continued

EFFECT OF DEFAUNATION USING COMPOUNDS
27, 30 AND 37 (BASED ON TABLE 1) ON SHEEP

| Measurement | Sampling Structure | | |
|---|---|---|---|
| | Pre-dose | 1 Week | 3 Week |
| Feed Intake (g/day) | 887 | 625 | 740 |
| COMPOUND 37 | | | |
| Protozoal Nos. (per mL × 10$^3$) | 497 | 0 | 0 |
| Bacterial gas production (Ml per 5 hr) | 1.8 | 1.9 | 3.4 |
| Feed Intake (g/day) | 1000 | 930 | 820 |

Dose Level: 167 mg/kg

EXAMPLE 10

Pilot Field Testing

In this trial the effect of defaunation agents after 1 and 2 weeks was examined in sheep in pilot field studies.

Thirty mature fine wooled merino weather sheep consuming a forage diet were given a single dose of either compound 27 or 37. The dose rate was 167 mg/kg and each compound was dispersed in 20 mL of ethanol and 200 mL of centrifuged rumen liquor. The compounds were then administered into the rumen using a flexible stomach tube. One week after dosing, total elimination of protozoa in all sheep was achieved. The sheep showed no adverse effects and grazing behavior was normal.

The effect of defaunation is summarized in Table 5. The results show complete elimination of protozoa can be achieved in the field 1 week after dosing.

TABLE 5

ELIMINATION OF PROTOZOAL POPULATION
IN SHEEP HELD IN PILOT FIELDS

| | Protozoal number (per mL × 10$^3$) | | | |
|---|---|---|---|---|
| Compound | Week 0 | Week 1 | Week 2 | Week 3 |
| 27 | 285 | 0 | 0 | 0 |
| 37 | 190 | 0 | 0 | 0 |

EXAMPLE 11

Liveweight Gain—Lambs

Three cross-bred lambs were defaunated with compound 37 at dose rate of 332 mg per kg liveweight. The lambs were allowed four weeks to adapt to defaunation before commencing the trial. The lambs were grazed at pasture. Ten control (faunated) cohorts of the defaunated group, which were matched for liveweight, were grazed in the same paddock, but separated from the defaunated lambs by a double-fence (4 meter separation). This was to prevent the faunated lambs contaminating the defaunated lambs. Both groups of lambs were weighed on four occasions at three weekly intervals. Protozoa were also monitored at the same time. Table 6 clearly demonstrates a highly significant improvement in the rate of liveweight gain ($P<0.01$) of the defaunated lambs over the controls.

TABLE 6

THE EFFECT OF TREATMENT WITH COMPOUND 37 FROM
TABLE 1 ON PROTOZOAL POPULATION NUMBER AND
LIVE WEIGHT ON GROWING LAMBS.

| Treatment | Measurement | Time (Weeks) | | | | | ADG (g/d) | Increase (%) |
|---|---|---|---|---|---|---|---|---|
| | | 0 | 3 | 6 | 9 | 12 | | |
| Control | *Liveweight (kg) | 24.2 | 26.5 | 28.5 | 30.7 | 32.3 | 100 | 0 |
| | Protozoal numbers (per mL × 10$^3$) | 536 | 455 | 427 | 374 | 334 | | 72 |
| Defaunated Compound No. 37 | *Liveweight (kg) | 24.8 | 28.0 | 31.2 | 35.7 | 38.7 | 165 | 65 |
| | Protozoal numbers (per mL × 10$^3$) | 0 | 0 | 0 | 0 | 0 | | |

Non-fasted liveweight

EXAMPLE 12

Effect of Compound 37 (From Table 1) on the Growth and Carcass Measurements in Lambs Three cross-bred lambs were defaunated with compound 37 at dose rate of 332 mg per kg liveweight. The lambs were allowed four weeks to adapt to defaunation before commencing the trial. The lambs were grazed at pasture. Then control (faunated) cohorts of the defaunated group, which were matched for liveweight, were grazed in the same paddock, but separated from the defaunated lambs by a double-fence (4 meter separation). This was to prevent the faunated lambs contaminating the defaunated lambs.

At 16 weeks post-defaunation both groups of the lambs were sacrificed and measurements taken.

Table 7 shows the cold carcass weight expressed as a percentage of the non-fastened liveweight. Also shown is the cross-sectional area of the longissimus dorsi (loin eye muscle) measured between the 12th and 13th rib. Generally, the table demonstrates an increase in lean meat yield as a result of defaunation.

TABLE 7

EFFECT OF COMPOUND 37 ON THE GROWTH AND CARCASS MEASUREMENTS IN LAMB

| MEASURE- MENT | TREATMENT | | |
|---|---|---|---|
| | CONTROL | DEFAUN- ATION | RESPONSE TO DEFAUN. (%) |
| ADG (g/d) | 96 | 165 | 72** |
| CARCASS DRESSING OUT PERCENTAGE | 38.5 | 44.5 | 16** |
| LOIN EYE MUSCLE AREA (CM²) | 9.9 | 12.5 | 26** |

ADG = AVERAGE DAILY GAIN.
**p < 0.01

EXAMPLE 13

Cattle Defaunation

Four cattle each were defaunated using either compounds No. 27 or No. 37 at a dose rate of 332 mg/kg. The compounds were administered by firstly mixing with 100 mL of ethanol and then adding 400 mL of centrifuged rumen liquor. This mixture was then administered into the rumen of the animal using a stomach tube. Table 8 demonstrates that these compounds are able to eliminate protozoa from cattle.

TABLE 8

THE EFFECT OF ADMINISTERING COMPOUNDS 27 AND 37 (FROM TABLE 1) ON MEAN PROTOZOAL NUMBERS IN RUMEN IN CATTLE

| Treatment | Protozoal Number (per mL × 10³) Time Weeks | |
|---|---|---|
| | Week 0 | Week 4 |
| Control | 190 | 500 |
| Defaunated, compound 27 | 220 | 0 |
| Defaunated, compound 37 | 313 | 0 |

EXAMPLE 14

Improved Efficacy of Defaunation Using 2 or 3 Repeated Doses in Sheep

Sheep were fed a diet of 900 g oaten chaff daily, except that food and water were withheld for 19 hours before and 24 hours after dosing. Each dose was prepared by mixing compound 37 with 20 ml of ethanol followed by 200 ml of centrifuged rumen liquor, to give a dose of 167 mg/kg body weight, administered by rumen tube. Rumen protozoa were counted weekly following the final treatment.

Table 9: The effect of administering compound 37 (from table 1) on mean protozoal numbers in rumen in sheep.

The results, presented in Table 9 shows that where the single dose failed to eradicate in three out of three sheep a regime of 2 or 3 repeated doses was fully effective.

| Protozoal Count (number/mL of rumen fluid) Compound: No. 37 | | | | | |
|---|---|---|---|---|---|
| Sheep | Time (weeks) | | | | |
| Tag No. | 0 | 1 | 2 | 3 | 4 |
| Dose 167 mg/kg | | | | | |
| 1253 | 151,500 | 0 | 370,000 | N/A | N/A |
| 1247 | 300,000 | 0 | 0 | 88,800 | N/A |
| 1073 | 149,500 | 0 | 4,500 | N/A | N/A |
| (2 doses, 1 wk apart) (at 167 mg/kg/dose) | | | | | |
| 1701 | 64,000 | 0 | 0 | 0 | 0 |
| 1121 | 68,500 | 0 | 0 | 0 | 0 |
| 1236 | 94,000 | 0 | 0 | 0 | 0 |
| (3 doses, 1 wk apart) (at 167 mg/kg per dose) | | | | | |
| 1110 | 259,000 | 0 | 0 | 0 | 0 |
| 1708 | 242,500 | 0 | 0 | 0 | 0 |
| 1235 | 122,500 | 0 | 0 | 0 | 0 |

N.B.
Protozoal count of "0" means none detectable.
One protozoan detected is equivalent to 500/ml of rumen fluid.

EXAMPLE 15

Reliability of Defaunation Using 2 Repeated Doses in Sheep

Sixty (60) Sheep, in three successive trials of 20 each, were treated with 2 doses of compound 37, one week apart, according to the method of Example 14. Protozoa were counted at 4 or 5 weeks after the second treatment.

TABLE 10

The effect of administering compound 37 (from Table 1) on mean protozoal numbers in rumen in sheep.
Protozoal Count*¹ (number/ml of rumen fluid)
Compound: No. 37

| Sheep | doses, 1 wk apart (at 167 mg/kg/dose) Time (weeks) | | | | |
|---|---|---|---|---|---|
| Tag No. | 0 | 1 | 2 | 3 | 4 |
| Group 1 (19 Sheep) | 345,000 | | | | 79*² |
| Group 2 (20 Sheep) | 207,000 | | | | 0 |
| Group 3 (18 Sheep) | 463,000 | | | | 0 |

*¹average protozoal count over the entire population in each group.
*²one sheep had a residual protozoal population which showed unusually slight recovery at 4 weeks.

I claim:
1. A method for defaunation of a ruminant animal, the method comprising administering to said animal an effective amount of a compound comprising a structure:

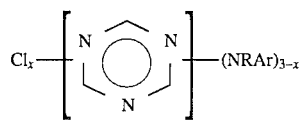

wherein:
X is 1 or 2;

R is H or lower alkyl; and

Ar is phenyl, diphenyl, naphthyl, anthracyl, phenanthryl, or a substituted derivative thereof, wherein said substituents are selected from the group consisting of $C_1$–$C_{12}$ aliphatic hydrocarbyl, aryl, nitroso, nitro, amino, chloro, bromo, iodo, hydroxyl, azo, cyano, thiocyano, aryloxy, alkoxy, mercaptyl and thioether, wherein aryl is phenyl, diphenyl, naphthyl, anthracyl, or phenanthryl.

2. The method of claim 1, said compound comprising a structure:

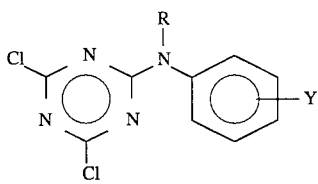

wherein

R is H or lower alkyl; and

Y is selected from the group consisting of $C_1$–$C_{12}$ aliphatic hydrocarbyl, aryl, nitroso, nitro, amino, chloro, bromo, iodo, hydroxyl, azo, cyano, thiocyano, aryloxy, alkoxy, mercaptyl and thioether, wherein aryl is phenyl, diphenyl, naphthyl, anthracyl, or phenanthryl.

3. The method of claim 2, wherein said compound is 2,4-dichloro-6-(2-chloroanilino)-1,3,5-triazine.

4. The method of claim 2, wherein said compound is 2,4-dichloro-6-(2,4-dimethylanilino)-s-triazine.

5. The method of claim 2, wherein said compound is 2,4-dichloro-6-(3-chloro-4-methylanilino)-s-triazine.

6. The method of claim 2, wherein said compound is 2,4-dichloro-6-(p-chloroanilino)-s-triazine.

7. The method of claim 2, wherein said compound is 2,4-dichloro-6-(p-bromoanilino)-s-triazine.

8. The method of claim 2, wherein said compound is 2,4-dichloro-6-(p-toluidino)-s-triazine.

9. The method of claim 2, wherein said compound is 2,4-dichloro-6-(p-anisidino)-s-triazine.

10. The method of claim 2, wherein said compound is 2,4-dichloro-6-(3,4-dichloroanilino)-s-triazine.

11. The method of claim 2, wherein said compound is 2,4-dichloro-6-(3,4-xylidino)-s-triazine.

12. The method of claim 2, wherein said compound is 2,4-dichloro-6-(3-(methylthio)-anilino)-s-triazine.

13. The method of claim 2, wherein said compound is 2,4-dichloro-6-(4-(methylthio)-anilino)-s-triazine.

14. The method of claim 2, wherein said compound is 2,4-dichloro-6-(3-cyanoanilino)-s-triazine.

15. The method of claim 2, wherein said compound is 2,4-dichloro-6-(4-tert-butylanilino)-s-triazine.

16. The method of claim 2, wherein said compound is 2,4-dichloro-6-(4-isopropylanilino)-s-triazine.

17. The method of claim 2, wherein said compound is 2,4-dichloro-6-(3-iodoanilino)-s-triazine.

18. The method of claim 2, wherein said compound is 2,4-dichloro-6-(3,4,5-trichloroanilino)-s-triazine.

19. The method of claim 2, wherein said compound is 2,4-dichloro-6-(3-chloro-p-toluidine)-s-triazine.

20. The method of claim 2, wherein said compound is 2,4-dichloro-6-(2,4-xylidino)-s-triazine.

21. The method of claim 2, wherein said compound is 2,4-dichloro-6-(2,4-dichloroanilino)-s-triazine.

22. The method of claim 1, wherein the compound is combined with an agent selected from the group consisting of non-toxic liquid solvents, co-solvent for dispersion of the compound, anti-foaming agent, emulsifier, suspending agent, surfactant, buffer or preservative.

23. The method of claim 22, wherein said non-toxic liquid solvent is water.

24. The method of claim 22, wherein said co-solvent for dispersion of the compound is selected from the group consisting of ethanol, DMSO and N-methyl pyrrolidone.

25. The method of claim 22, wherein said suspending agent is selected from the group consisting of carboxymethylcellulose, xanthan gum and polymeric silicone based agents.

26. The method of claim 22, wherein said surfactant is any food grade surfactant or ethoxylated castor oil.

27. The method of claim 22, wherein said buffer, buffers the pH to between 4 and 8.

28. The method of claim 22, wherein said preservatives are selected from the group consisting of methyl paraben, propyl paraben and sorbic acid.

29. The method of claim 1, wherein said compound is administered at a dose from 1 to 1000 mg compound per kg of animal body weight.

30. The method of claim 29, wherein said compound is administered at a dose from 10 to 340 mg/kg.

31. The method of claim 29, wherein said compound is administered at a dose of from 70 to 170 mg/kg.

32. The method of claim 29, wherein said compound is administered at a dose of from 80 to 85 mg/kg.

33. The method of claim 29, wherein said compound is administered in a single dose.

34. The method of claim 29, wherein said compound is administered in a form suitable for short duration sustained release.

35. The method of claim 29, wherein said compound is administered in pulse releases.

36. The method of claim 35, wherein the pulse releases are carried out every 2 to 8 months.

37. The method of claim 35, wherein the pulse releases are carried out every 2 to 6 months.

38. The method of claim 35, wherein the pulse releases are carried out every 2 to 3 months.

39. The method of claim 29, wherein said animal is re-dosed every 1 to 12 months.

40. The method of claim 29, wherein said animal is re-dosed every 2 to 8 months.

41. The method of claim 29, wherein said animal is re-dosed every 5 to 7 months.

42. The method of claim 29, wherein the compound is administered in repeated dosages over a 2-day to 6-day week interval.

43. The method of claim 34, wherein said compound is combined with wax and iron filings or gelatin.

44. The method of claim 1, wherein said compound is administered in a form selected from the group consisting of liquid, capsule, tablet and powder.

45. The method of claim 44, wherein said compound is administered orally.

46. The method of claim 1, wherein the defaunation compound is combined with said animal's feed.

47. The method of claim 1, which further comprises the step of separating defaunated animals from other animals.

48. The method of claim 1, wherein said compound is effective in reducing rumen fungal populations.

49. The method of claim 1, wherein said animal is a sheep.

50. The method of claim 1, wherein said animal is a bovine.

51. The method of claim 1, wherein the aliphatic hydrocarbyl is a lower alkyl.

52. The method of claim 2, wherein the aliphatic hydrocarbyl is a lower alkyl.

53. The method of claim 1, wherein Ar is phenyl or a substituted derivative thereof.

* * * * *